(12) United States Patent
Minter et al.

(10) Patent No.: US 9,696,303 B2
(45) Date of Patent: Jul. 4, 2017

(54) ASSAY DEVICE

(75) Inventors: Stephen John Minter, Derbyshire (GB); Georgios Patsos, Derbyshire (GB)

(73) Assignee: REVOLUGEN LIMITED, New Mills (GB)

(*) Notice: Subject to any disclaimer, the term of this patent is extended or adjusted under 35 U.S.C. 154(b) by 392 days.

(21) Appl. No.: 13/879,500

(22) PCT Filed: Oct. 17, 2011

(86) PCT No.: PCT/GB2011/001487
§ 371 (c)(1),
(2), (4) Date: Jul. 8, 2013

(87) PCT Pub. No.: WO2012/049465
PCT Pub. Date: Apr. 19, 2012

(65) Prior Publication Data
US 2013/0280699 A1    Oct. 24, 2013

(30) Foreign Application Priority Data

Oct. 15, 2010    (GB) .................................. 1017447.2

(51) Int. Cl.
*G01N 33/543*    (2006.01)
*G01N 33/558*    (2006.01)

(52) U.S. Cl.
CPC ..... *G01N 33/54366* (2013.01); *G01N 33/558* (2013.01); *G01N 33/543* (2013.01); *G01N 33/54306* (2013.01)

(58) Field of Classification Search
None
See application file for complete search history.

(56) References Cited

U.S. PATENT DOCUMENTS 5,910,406 A    6/1999    Minter et al.
6,020,209 A *    2/2000    Narang ............ G01N 33/54366
                                                            422/504

(Continued)

FOREIGN PATENT DOCUMENTS

CN    101305282    11/2008
JP    9-503581    4/1997

(Continued)

OTHER PUBLICATIONS

Singapore Office Action dated May 9, 2014, issued in connection with Singapore Application No. 201302819-6.

(Continued)

*Primary Examiner* — Rebecca Martinez
(74) *Attorney, Agent, or Firm* — Nixon & Vanderhye P.C.

(57) ABSTRACT

An assay device (1) for determining the presence and/or amount of an analyte present or potentially present in a liquid sample comprises: (i) a capillary tube (2) having an upstream region (3) into which the sample to be assayed is introduced for transfer by capillary action along the capillary tube to a downstream region thereof; (ii) a collection of first binding partners (5) immobilized within the capillary tube (2), said first binding partners (5) being capable of specifically binding to the analyte; (iii) a collection of second binding partners (6) displaceabley bound to a fraction of said first binding partners (5) whereby there are free first binding partners (5) immobilized within the capillary tube, said second binding partners (6) having a label and being displaceable from the first binding partners (5) by the analyte to be detected; and (iv) a detection region (4) for sample that has transferred to said downstream region of said capillary tube, said detection region being adapted to generate a detectable signal from the label on displaced second binding partners (6) that have transferred to the downstream region.

8 Claims, 8 Drawing Sheets

(56) References Cited

U.S. PATENT DOCUMENTS

| 6,323,042 | B1 | 11/2001 | Narang et al. |
|---|---|---|---|
| 2004/0005582 | A1 | 1/2004 | Shipwash |
| 2005/0247563 | A1* | 11/2005 | Shuber ............ G01N 27/44713 204/450 |
| 2006/0194342 | A1 | 8/2006 | Bond et al. |
| 2008/0248504 | A1 | 10/2008 | Ruddell et al. |
| 2009/0035743 | A1 | 2/2009 | Minter et al. |
| 2009/0181442 | A1 | 7/2009 | Banuls Polo et al. |
| 2010/0062544 | A1 | 3/2010 | Evans et al. |

FOREIGN PATENT DOCUMENTS

| WO | WO 93/13220 A1 | 7/1993 |
|---|---|---|
| WO | WO 95/06240 A1 | 3/1995 |
| WO | WO 97/25619 | 7/1997 |
| WO | WO 00/33063 | 6/2000 |
| WO | WO 2006/046054 | 5/2006 |

OTHER PUBLICATIONS

Li et al, "A new class of homogeneous nucleic acid probes based on specific displacement hybridization", Nucleic Acids Research, 2002, vol. 30, No. 2 e5, pp. 1-9.
Sheikh et al, "Development of a Fluorescence Immunoassay for Measurement of Paclitaxel in Human Plasma", Analytical Biochemistry 283, 33-38 (2000).
Communication from European Patent Office (EP Application No. 11 788 549.1, Applicant: Moorlodge Biotech Ventures Limited, Title: Assay Device, Inventor: Minter et al) dated Sep. 27, 2016.
International Search Report for PCT/GB2011/001487, mailed Mar. 8, 2012.
Mastichiadis, C. et al., "Capillary-based immunoassays, immunosensors and DNS sensors—steps towards integration and multi-analysis", TRAC, Trends in Analytical Chemistry, vol. 27, No. 9, (Oct. 1, 2008), pp. 771-784.
Ho, F.M. et al., "A strand exchange FRET assay for DNA", Biosensors and Bioelectronics, vol. 20, No. 5, (Nov. 15, 2004), pp. 1001-1010.
Charles, P.T. et al., "Microcapillary reversed-displacement immunosensor for trace level detection of TNT in seawater", Analytica Chemica Acta, vol. 525, No. 2, (Nov. 8, 2004).
Narang, U. et al., "Multianalyte detection using a capillary-based flow immunosensor", Analytical Biochemistry, vol. 255, No. 1, (Jan. 1, 1998), pp. 13-19.
Sheikh, S.H. et al., "Development of a fluorescence immunoassay for measurement of paclitaxel in human plasma", Analytical Biochemistry, vol. 283, No. 1, (Jul. 15, 2000), pp. 33-38.
European Examination Report dated Mar. 25, 2015, issued in connection with European Patent Application No. 11 788 549.1.
Yu H et al, "Use of the USDT flow immunosensor for quantitation of benzoylecgonine in urine", Biosensors and Bioelectronics, vol. 11, No. 8, Jan. 1, 1996, pp. 725-734.
English translation of Japanese Office Action dated Jun. 30, 2015, issued in connection with Japanese Patent Application No. 2013-533276.
English translation of Chinese Office Action dated Jan. 2, 2014, issued in connection with Chinese Patent Application No. 201180059831.0.

* cited by examiner

ASSAY DEVICE

This application is the U.S. national phase of International Application No. PCT/GB2011/001487, filed 17 Oct. 2011, which designated the U.S. and claims priority to GB Application No. 1017447.2, filed 15 Oct. 2010, the entire contents of each of which are hereby incorporated by reference.

The present invention relates to an assay device for use in determining the presence and/or amount of a particular analyte in a liquid sample. The invention has particular (but not exclusive) application to the analysis of biological samples and is particularly useful for medical diagnosis applications. The device may be used, for example, for analysing a liquid sample (e.g. a body fluid such as blood, urine, CSF or sputum or one prepared from tissue, e.g. by homogenisation) from a patient to determine the presence and/or amount of an analyte, e.g. organisms (bacteria, parasite or virus etc) which are foreign to the human body or the presence of cells of a particular type (e.g. tumour cells), thereby providing a diagnosis of a medical condition.

Medical diagnosis is, of course, a well advanced science. Many such diagnoses of samples (e.g. blood, urine, CSF, tissue and sputum) from patients are routinely carried out by hospitals, doctors surgeries and other medical centres every day. Many such diagnoses require that the sample be taken from a patient and sent to a laboratory (which may be on the premises of the medical centre) for an analysis procedure. By example only, methods are available that are used in a centralised laboratory by trained staff that are based upon PCR. Such methods often require interpretation of the results (this is true particularly when q PCR is the test system) that are obtained and if not performed correctly can produce misleading results since any nucleic acid amplification system has the possibility that it can produce a mismatch that once formed results in an amplified negative (abortive) signal. Furthermore such methods frequently require lengthy gel development steps or column separation steps to obtain the result, which may then require skilled interpretation. Consequently some considerable time may elapse between the time when the sample is taken and the result is available to the medical practitioner who can then prescribe any necessary treatment.

It is therefore an object of the present invention to obviate or mitigate the above mentioned disadvantages.

According to a first aspect of the present invention there is provided an assay device for determining the presence and/or amount of an analyte present or potentially present in a processed liquid sample, the device comprising:
(i) a capillary tube having an upstream region into which the sample to be assayed is introduced for transfer by capillary action along the capillary tube to a downstream region thereof;
(ii) a collection of first binding partners immobilised within the capillary tube, said first binding partners being capable of specifically binding to the analyte;
(iii) a collection of second binding partners displaceabley bound to a fraction of said first binding partners whereby there are free first binding partners immobilised within the capillary tube, said second binding partners having a label and being displaceable from the first binding partners by the analyte to be detected; and
(iv) a detection region for sample that has transferred to said downstream region of said capillary tube, said detection region being adapted to generate a detectable signal from the label on displaced second binding partners that have transferred to the downstream region.

According to a second aspect of the present invention there is provided a method of assaying a liquid sample for determining the presence and/or amount of an analyte present or potentially present in the sample, the method comprising the steps of:
(a) providing a capillary tube having immobilised therein a collection of first binding partners capable of specifically binding to the analyte, said capillary tube further incorporating a collection of second binding partners displaceabley bound to a fraction of said first binding partners whereby there are free first binding partners immobilised within the capillary tube, said second binding partners having a label and being displaceable from the first binding partners by the analyte to be detected;
(b) causing the liquid sample to flow from an upstream end of the capillary tube to a downstream end thereof; and
(c) detecting for the presence of the label at the downstream end of the capillary tube.

In the following description, features described in relation to the assay device of the invention (i.e. the "first aspect") are to be considered applicable mutatis mutandis to the method ("second aspect") of the invention and vice versa.

The assay device of the invention is capable of detecting the presence and/or amount of a particular analyte present or potentially present in a sample without giving "false positives". The basis of the invention lies in the use of the immobilised first binding partners and second binding partners that are displaceably bound thereto. There are two important features in relation to the first binding partners. The first is that they may be highly specific to the analyte to be determined. Secondly, a fraction (less than 100%) of the immobilised first binding partners have the labelled second binding partners displaceably bound thereto. Given that the sample to be analysed contains the particular analyte of interest then this analyte will displace the second binding partners from the (immobilised) first binding partners and they (the second partners) will be transferred by the capillary flow to the detection region where the label will cause a detectable signal to be produced. Detection of the signal is confirmation that the particular analyte was present in the sample. On the contrary, if the particular analyte is not present in the sample then (at least in an idealised case) there will be no displacement of the second binding partners from the (immobilised) first binding partners and consequently no signal can be generated at the detection region. However, in practice, it is possible that one or more components in a sample being analysed (which does not otherwise contain the particular analyte under investigation) may have a low probability of displacing some second binding partners. Should this happen, the displaced second binding partners will be "trapped" by one or other of the fraction of the immobilised first binding partners that do not have a second binding partner bond thereto. Consequently in this case where there has been some initial displacement of second binding partners none will reach the detection region and therefore no signal is generated. In the idealised cases described so far, it has been assumed that labelled, second binding partner can only reach the detection region if displaced by the target analyte. However we do not exclude the possibility that labelled, second partner displaced by species in the sample other than the target analyte will ultimately reach the detection region. In this case, two possibilities may be envisaged. The first is that the sample does contain the target analyte, in which case signal produced by labelled second binding partners displaced by the target analyte will be much greater than any signal produced by labelled second binding partners displaced by "non-target" analyte. In the second case, there is no target analyte in the sample, in which case any labelled, second binding partners displaced by "non-target" analyte will only give rise to a very low signal. It is possible to take account of these two cases by detecting for signal only above a particular intensity and/or running a control capillary (see infra) in which case the signal from the detection region of the control capillary may be "subtracted" from that produced at the detection region of the "assay capillary" to provide a net signal for the latter. Thus "false positives" are avoided.

The assay device of the invention is particularly useful for the analysis of aqueous samples and has particular applicability to medical samples (e.g. blood, sputum CSF or urine) to determine the presence therein of a target analyte which would be indicative of a particular medical condition afflicting a patient from whom the sample was taken. If necessary, such medical samples may be subjected to a standard lysis procedure before being subjected to the analysis, particularly in the case where the target analyte is a nucleic acid see infra. Alternatively or additionally the sample may be diluted with water or buffer (e.g. PBS) to reduce its viscosity to allow for capillary flow.

In preferred embodiments of the invention, the device will additionally comprise a control capillary tube into which a fraction of the sample is introduced for transfer by capillary action along the control capillary tube to a downstream region thereof. Such an embodiment will further comprise a detection region for sample that has been transferred along the control capillary tube to the downstream region thereof. In this embodiment, the control capillary tube is devoid of second binding partners. For the purposes of determining the result of an analysis, the detection regions of the "assay" capillary tube and the "control capillary tube" maybe compared to determine the net signal resulting from the former.

Preferably 10-90% by mole, more preferably 50-70% by mole, of the first binding partners have second binding partners bound thereto.

Generally there will be at least 10 μmol of first binding partners in the capillary tube. Ideally there are more molecules of second binding partners in the capillary than there are target molecules in the sample otherwise generated signal may plateau (as explained with reference to FIG. 1 below).

Preferably the first binding partners are covalently immobilised within the capillary tube.

The first and second binding partners may take a number of forms. Thus, in one embodiment of the invention, the (immobilised) first binding partners may comprise nucleic acid sequences and the labelled, second binding partners may also comprise nucleic acid sequences hybridised thereto. The nucleic acid sequences may comprise DNA, RNA, mRNA or PNA (Protein Nucleic Acid) sequences. The immobilised, nucleic acid sequence may be one selected so as to be specifically hybridisable to (at least part of) a target nucleic acid sequence which is potentially present in the sample to be assayed. Thus the first binding partner will have a sequence which is ideally fully complementary to a sequence which is characteristic of the target nucleic acid. It will however generally be preferred that there is a degree of mismatch between the sequence of the immobilised nucleic acid and that of the labelled nucleic acid. This will ensure that the labelled nucleic acid is displaceable from the immobilised nucleic acid by the target nucleic acid. Generally there will be at least 60%, but usually less than 100%, sequence homology between the immobilised nucleic acid and the labelled nucleic acid.

In the case of a sample from a patient, (e.g. blood, urine CSF or sputum) the target nucleic acid may be one that is characteristic of a particular organism (e.g. bacteria, parasite or virus) with which the patient may be infected. Thus, in this case, the test is carried out as a diagnosis of whether the patient is afflicted by that organism. The target nucleic acid sequence may for example be present in chromosomal or plasmid DNA. Alternatively the nucleic acid may be one that is characteristic of malignant tissue (tumour cell).

The assay device of the invention is applicable to diagnosis of a wide range of medical conditions by testing for the presence of a particular nucleic acid sequence (characteristic of the medical condition) present in a sample taken from the patient. Purely by way of example, the assay device may be one for determining the presence (or otherwise) of the organism *Neisseria meningitides* which is known for its role in meningitis and other forms of meningococcal disease. In this case, the immobilised oligonucleotides (i.e. the "first binding partners") may be selected from:

```
                                              SEQ ID NO: 1)
         ATTTTAATTACGAAGGCTACGCATT;

SEQ ID NO: 2)
         GGGACACCCGCGAAGTTTTGGAAGC;

SEQ ID NO: 3)
         CTGTCAGTTGTCTCGTGCATTGTCA;

SEQ ID NO: 4)
         GTTGCGGGCTGTTGCGTCGGAAACC;

SEQ ID NO: 5)
         ATGGATAAGCGCGACCAGTTCGCCG;

SEQ ID NO: 6)
         GATGTGTTTGGCAATCATGGCTTG;

SEQ ID NO: 7)
         CACAAGTGATGCGTCCGAGCGTAA.
```

By way of a further example, the assay device may be one for diagnosing *Chlamydia* in a patient, in which case the immobilised oligonucleotides may be selected from the following:

```
                                              SEQ ID NO: 8)
         GAGAACCAGACTAAAGTTTCAA;

SEQ ID NO: 9)
         AAAAAACGGTCAAAGCGGAGTC;

SEQ ID NO: 10)
         ACAGATACTGCCTTCTCTTGG;

SEQ ID NO: 11)
         ATCTGCAGCAGGTTTCGTGG;

SEQ ID NO: 12)
         CAGGCTGCGTGGCGTTTT;

SEQ ID NO: 13)
         ACAAAATCTTCTGATTTTAATACAGC;

SEQ ID NO: 14)
         TCTTTTTCCTAACACCGCTTTGAA;

SEQ ID NO: 15)
         AACACTGCTTTGGATCGAGCTGTG.
```

As an alternative to the use of nucleic acid sequences, the first binding partner may comprise an antibody and the second binding partner may comprise a labelled antigen or a labelled antigen/antibody complex. The immobilised antibody which forms the first binding partner will be specific for a target antigen potentially present in a sample to be assayed. The immobilised antibody may, for example, be a monoclonal antibody. Non-limiting examples of monoclonal antibodies suitable for use in the invention are detailed below.

1. Clone number M2110184 from Fitzgerald against *Neisseria Gonorrhoeae* which shows no reactivity against *N. meningitides, Chlamydia trachomatis* or other *Neisseria* species.

2. 10C13A from Fitzgerald against *Chlamydia trachomatis*.

In the case of (2), the second binding partner may, for example, be a complex of an antigen and a labelled monoclonal antibody, e.g. labelled Monoclonal antibody M4020311 (Cat #10-C13A). In this case, the second binding partner which is displaced by target analyte (if present in the sample) is the complex of the antigen and the labelled monoclonal antibody.

Many other antibodies are commercially available from other suppliers to cover a range of pathogens.

A still further possibility is that the assay device of the invention may be for the detection of a particular organism (e.g. a bacterium) by virtue of the presence of a particular glycan on the surface of the organism. Lectins are glycan binding proteins. Both lectins and glycans are found on cell (mammalian, bacterial) surfaces, viruses, protozoa, cyanabacteria etc. Proteins with lectin activity come under different names, e.g. galectins, selectins etc for mammalian cells, adhesins for bacterial cells, hemagglutinins for viruses. Also plants are a rich source of a diverse family of lectins (thousands of members) that can be easily purified and used for cell glycophenotyping.

In such a device, for detecting a particular organism by virtue of the presence of a specific lectin (e.g. an adhesin in the case of a bacterium) on its surface, the immobilised first binding partner may be a polysaccharide to which the surface lectin of the organism is capable of binding and the labelled second binding partner displaceably bound thereto may (for example) be a plant lectin capable of binding to the polysaccharide but also capable of being displaced therefrom by stronger binding of the cell lectin.

For the purpose of detecting the label on the second binding partners that have been displaced from the first binding partners and reached the detection region, there may be provided in the detection region a reagent system capable of interacting with the label to generate a detectable signal. The label on the second binding partner may be an enzyme and the reagent system (in the detection region) may comprise a substrate for the enzyme. Alternatively (although less preferred) the reagent system may comprise an enzyme and the label is a substrate for the enzyme. In a further embodiment of the invention, the label may be a "direct" label, i.e. one which provides a signal itself without the need for a reagent system to develop a signal.

In particularly preferred embodiments of the invention, the detectable signal is a light signal, most preferably a colour change. Detection of a colour change at the detection region may be effected by a detection arrangement of type known per se. This arrangement may be one which detects reflected or transmitted light for the purpose of determining the colour change. If the assay device includes a "control" capillary with associated detection region then the detection arrangement may make measurements at the detection regions of both the "assay" capillary tube and the "control" capillary tube and compare the results to determine the net change produced by the assay capillary tube.

Examples of labels that may be employed for the purposes of the invention are included in the following table (Table 1):

TABLE 1

| Label attached to second binding partner | Substrate for signal generation |
|---|---|
| Alkaline Phosphatase | 1 2 Dioxoetane (chemiluminescent) D luciferin-O-Phosphate (Bioluminescent) BCIP/NBT—Blue colour |
| Horse radish peroxidise | Luminol |
| Acridinium Ester | No Substrate Required—Acridinium Ester is a direct chemiluminescent label |

Devices in accordance with the invention will generally be prepared from a substrate (preferably polycarbonate) which is produced with open-topped channels which (when covered) provide the capillary pathways. The substrate may be treated to effect immobilisation of the first binding partners and the channels then covered to complete the capillary pathways.

It is preferred that the first binding partners are covalently bound within the capillary tube.

Various immobilisation chemistries may be used. In a preferred embodiment of the invention, the surface of the substrate is treated so as to have free thiol groups (—SH) which are connected by means of a linker group to the surface of the substrate and which may then be reacted with an amino group of the binding partner to be immobilised. In the case where the substrate is polycarbonate, there may be an initial nitration reaction (so as to nitrate aromatic groups of the polycarbonate) followed by a subsequent reduction to convert the nitro groups to amino groups. These may subsequently be reacted with a compound comprising an alkylene group terminated, at one end, with a thiol group and, at the other end, with a group capable of reacting with the amino groups. Examples of this type of chemistry are disclosed, for example, in US 2009/0181442.

A further example of immobilisation chemistry that may be used is disclosed in U.S. Pat. No. 5,910,406 (Tepnel).

The invention will be further described by way of example only with reference to the accompanying drawings, in which:

FIG. 1 schematically illustrates a first embodiment of assay device in accordance with the invention;

Figure 4:
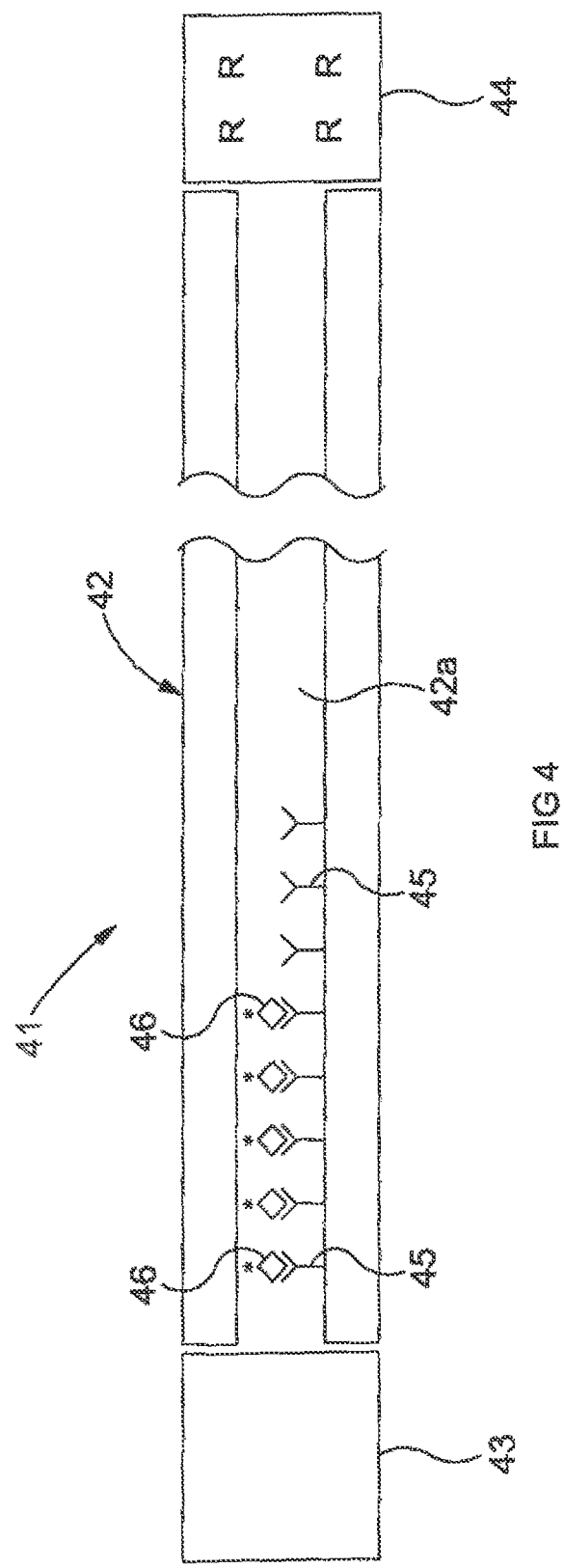
Figure 5:
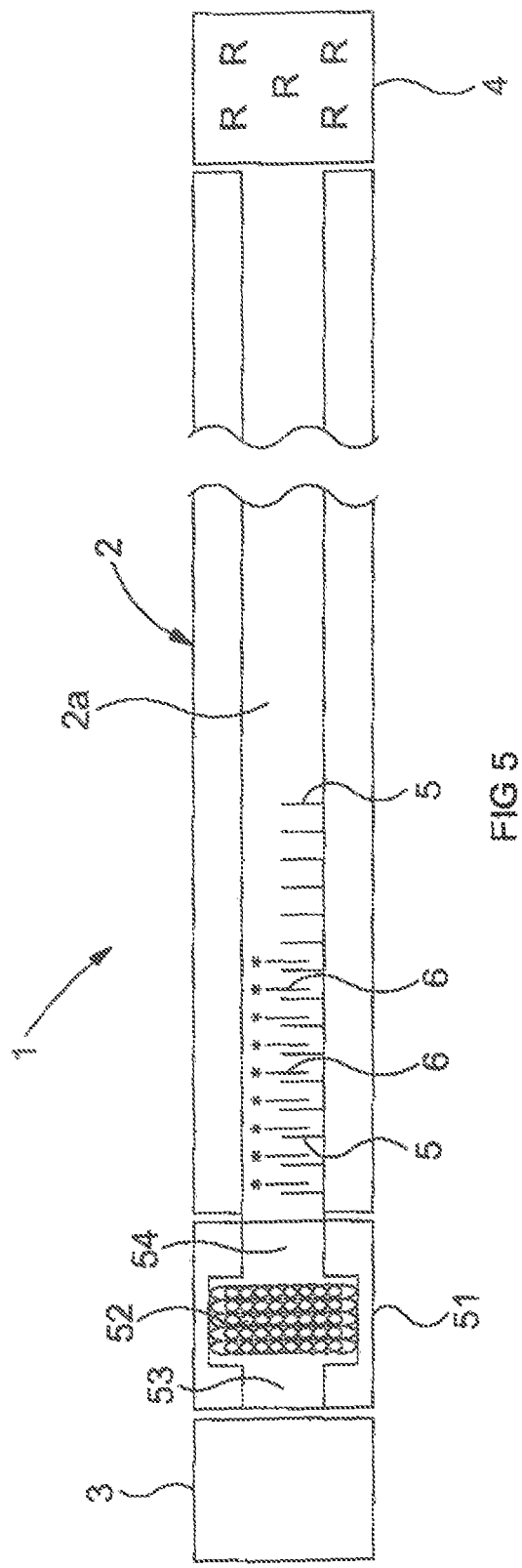
Figure 6:
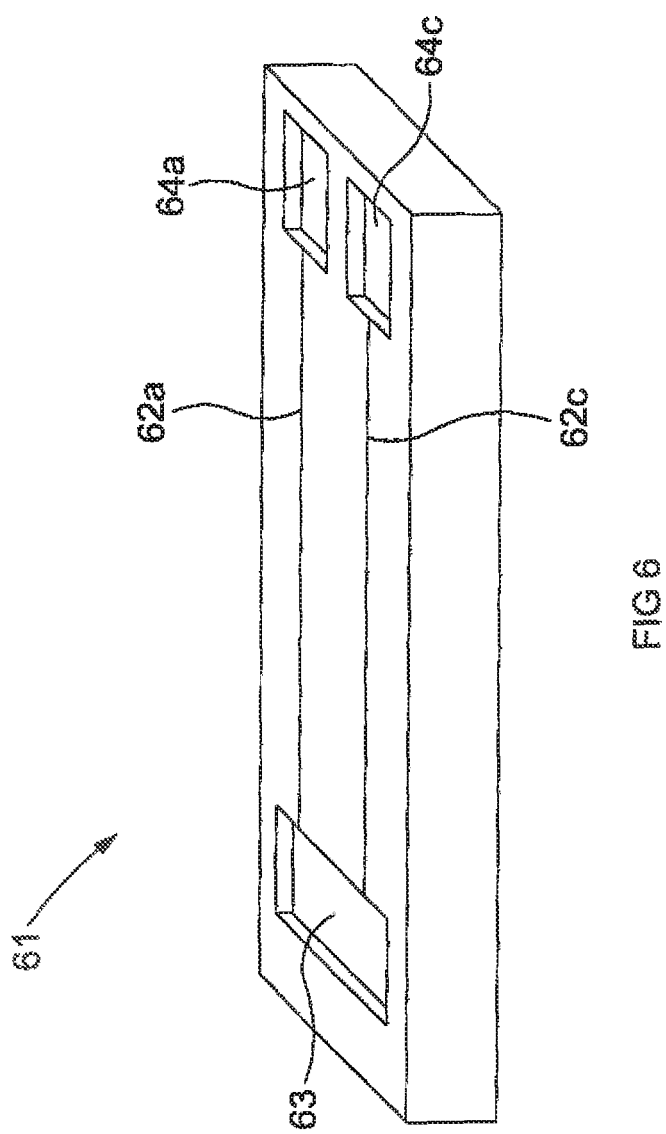
Figure 7:
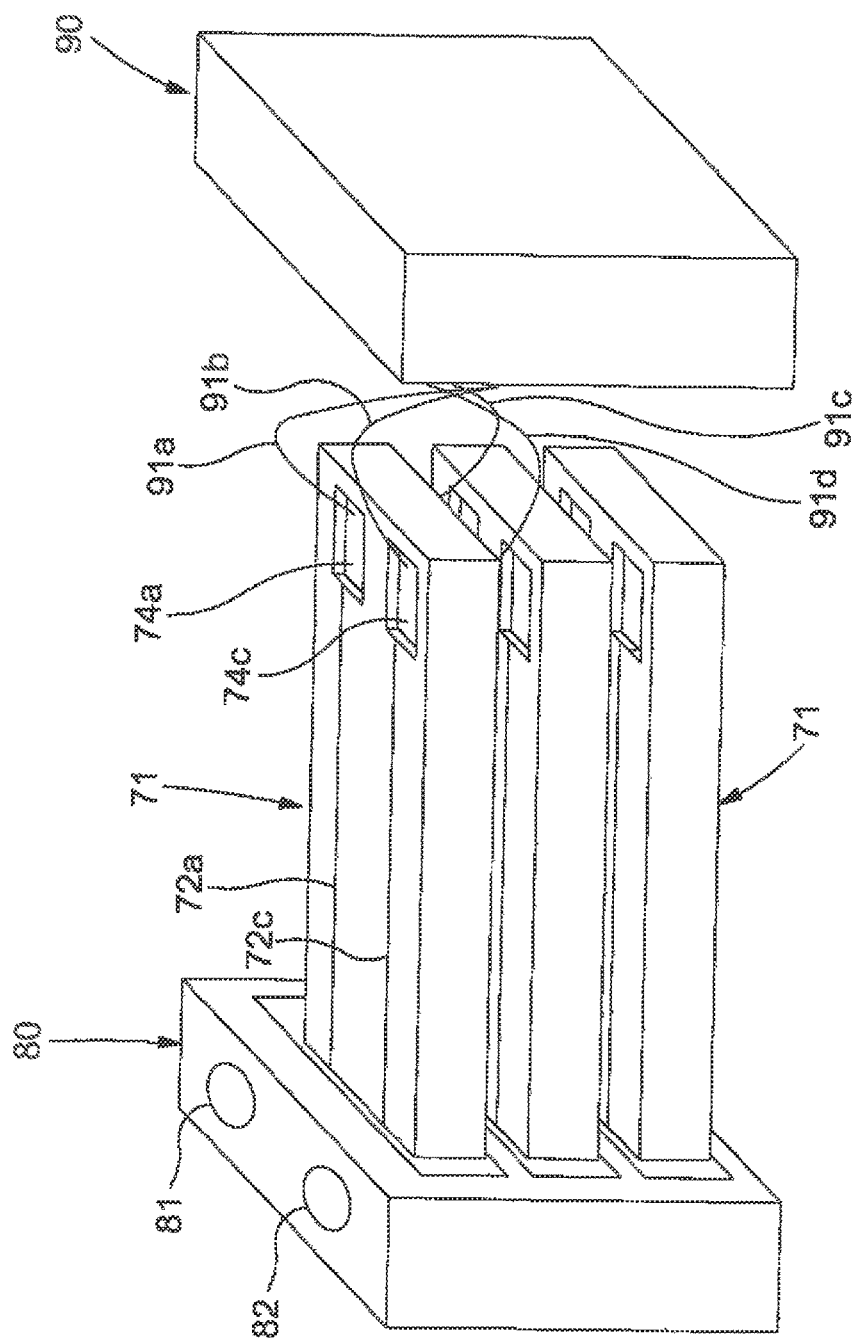

FIG. 4 schematically illustrates a second embodiment of assay device in accordance with the invention;

FIG. 5 is a schematic view of a third embodiment of assay device in accordance with the invention;

FIG. 6 schematically illustrates a moulding for producing an assay device in accordance with the invention;

FIG. 7 illustrates a further embodiment of the invention; and

Figure 8:
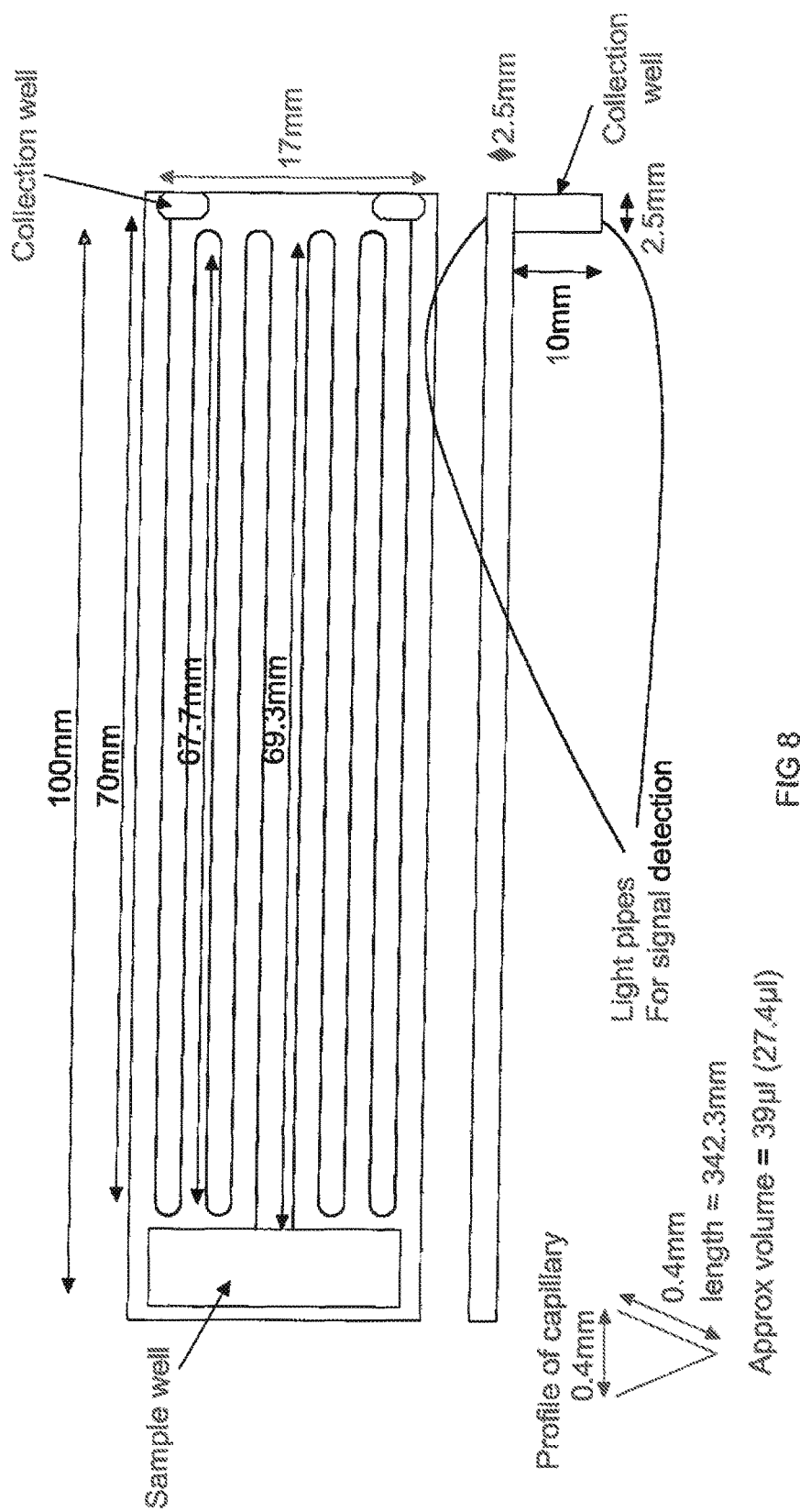

FIG. 8 shows plan and side views of a further embodiment of an assay device in accordance with the invention.

Figure 1:
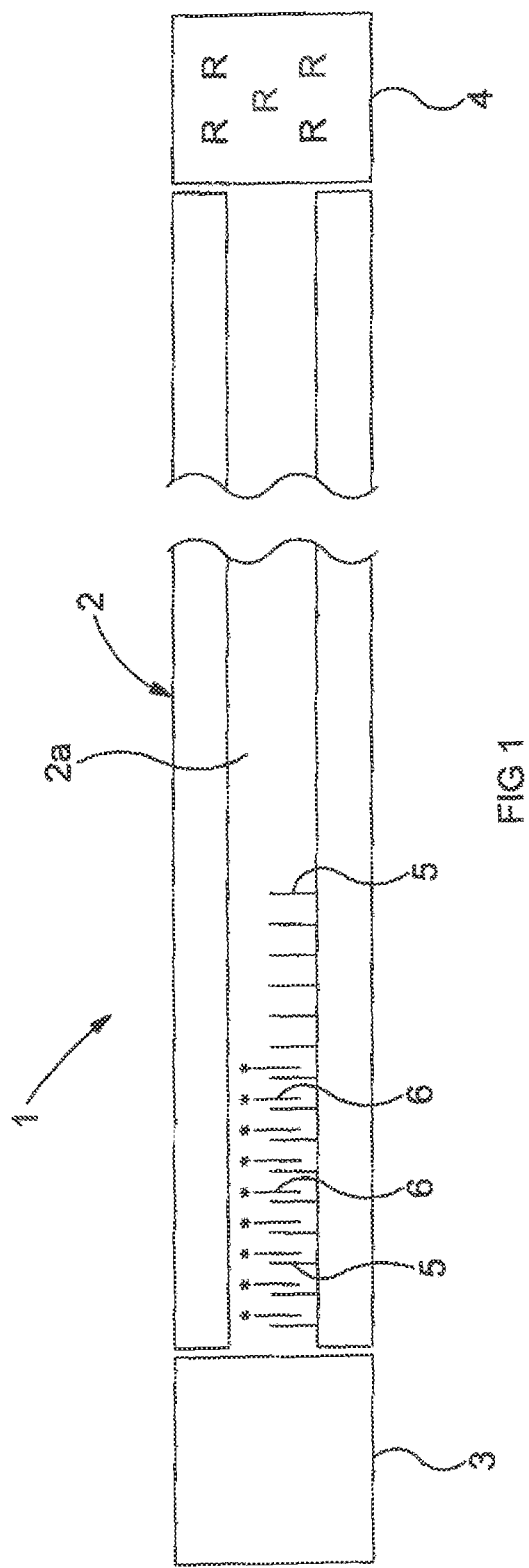

Reference is firstly made to FIG. 1 which schematically illustrates one embodiment of assay device 1 in accordance with the invention for analysis of a liquid sample to determine the presence therein of a nucleic acid (the "target nucleic acid") having a particular sequence of bases. The liquid sample may, for example, be a body fluid sample from a patient (e.g. blood, urine CSF, sputum or smear any one of which may be diluted as necessary to an appropriate viscosity) or may be one produced from a tissue biopsy (e.g. by homogenisation) from a patient. The sample may be one that is to be tested for the possible presence of a foreign organism (such as a bacteria, parasite or virus) having a particular nucleic acid sequence which is characteristic of that organism.

The illustrated device 1 comprises a capillary tube 2 (having a capillary bore 2a) associated with a sample receiving station 3 at its upstream end and a detection region 4 at its downstream end. Typically the capillary bore 2a will have a cross-sectional size in the range 0.1-0.5 mm. The sample receiving station 3 and detection region may, for example, comprise pads of absorbent material, for example, Whatman filter paper or Whatman Grade GF/B Glass Microfiber Filters, saturated with a buffer to maintain a particular pH characteristic, for example phosphate buffered saline. If the assay device is intended to detect a nucleic acid then the pad may contain a hybridisation buffer (e.g. 2×SSC (300 mM sodium chloride 30 mM sodium citrate). Formamide can be added to reduce the stringency of hybridisation (for example <50%)). The arrangement is such that liquid sample introduced at the sample receiving station 3 is able to pass into the upstream end of capillary bore 2a along which it then travels by capillary action to reach the detection region 4.

Provided over an upstream region of the capillary bore 2a is a collection of single-stranded oligonucleotides 5 (the "first binding partners") that are covalently immobilised on the wall of the capillary bore 2a. These oligonucleotides have a sequence which has 100% homology with a sequence in the target nucleic acid (and is therefore capable of specifically hybridising to the target nucleic acid) which is being assayed for in the sample (e.g. the nucleic acid that is characteristic of a particular bacteria or virus). For simplicity, the oligonucleotides 5 are shown as being arranged in a single line along the interior of the capillary bore 2a but it will be appreciated that, in practice, oligonucleotides 5 will be arranged both around the wall of the capillary bore 2a and longitudinally therealong. Generally the oligonucleotides will comprise a sequence of 15-40 bases. They can be bonded to the capillary by either their 5' or 3' ends. Many such oligonucleotide sequences which are capable of specifically binding to nucleic acids which are characteristic of organisms are known and are available from databases such as Genbank and are therefore not further described here, although a few specific examples are given elsewhere in the present specification.

The oligonucleotides 5 may be present over about the first 25% of the length of the capillary bore 2a but other values are possible and will generally be in the range 10-90%.

Further provided within the capillary bore 2a is a collection of labelled, single-stranded oligonucleotides 6 (the "second binding partners"), the label being indicated by the "*" symbol.

Labelled oligonucleotides 6 have some sequence homology (usually at least 60% but generally less than 100%) with the immobilised oligonucleotides 5 and, as depicted in FIG. 1, are hybridised to the immobilised oligonucleotides 5. That said, the number of labelled oligonucleotides 6 is only a fraction of the number of the immobilised oligonucleotides 5. Typically this fraction will be in the range 10% to 90% by mole ratio. All labelled oligonucleotides 6 are hybridised to an immobilised oligonucleotide 5 (there are no free labelled oligonucleotide 6 in the device) but there is a sub-collection of immobilised oligonucleotides 5 which are "free" in the sense that they do not have a labelled oligonucleotide 6 hybridised thereto. It is this proportion of "free" immobilised oligonucleotides 5 which are important in the device to prevent "false positives". The manner in which such "false positives" are avoided is described in more detail below.

Purely for the purposes of explanation, the sub-collection of immobilised oligonucleotides 5 not having labelled oligonucleotides 6 hybridised thereto is shown as being positioned downstream of the remaining immobilised oligonucleotides (i.e. those having labelled oligonucleotides 6 hybridised thereto).

Brief reference was made above to the detection region 4. At this detection region 4 there is provided a reagent R that will interact with the label "*" provided on the labelled oligonucleotides 6 so as to produce a detectable signal. Thus, for example, the label "*" on labelled oligonucleotide 6 may be an enzyme and the detection region incorporates a substrate for the enzyme, the combination of the enzyme and substrate being such that a detectable signal is produced. Although not illustrated in FIG. 1, detection station 4 will be associated with a detection arrangement capable of detecting the type of signal generated by interaction of the label on oligonucleotides 6 and the reagent at the detection region 4. In preferred embodiments of the invention, the signal generated is a light signal preferably a colour change. Detection of such a colour change may be by means of reflected, emitted or transmitted light.

The detection region 4 may take various forms. Thus, for example, the region may comprise an absorbent material impregnated with the reagent R. However in a more preferred embodiment of the invention, the detection region comprises a well or the like containing liquid or freeze dried reagent R. In this preferred embodiment, the device is configured so that the liquid that has reached the end of the capillary pathway is discharged into the well so that the label on any displaced binding partner can react with reagent R and produce a colour change for detection.

The manner in which the assay device 1 illustrated in FIG. 1 functions to determine whether or not a particular analyte (in this case the target nucleic acid of a particular sequence) is present in a liquid sample to be analysed will now be explained with reference to FIG. 2 in which the same reference numerals are used as in FIG. 1 to denote the same features. For the purposes of FIG. 2, it is assumed that the liquid sample 10 to be assayed has been taken from a patient infected with a particular organism in which the target nucleic acid is present and the assay device 1 is intended to detect the presence of that nucleic acid (schematically depicted by reference numeral 11) and hence confirm infection of the patient by that organism. Thus the immobilised oligonucleotides 5 have sequence homology with the nucleic acid strands 11 to be detected.

Figure 2:
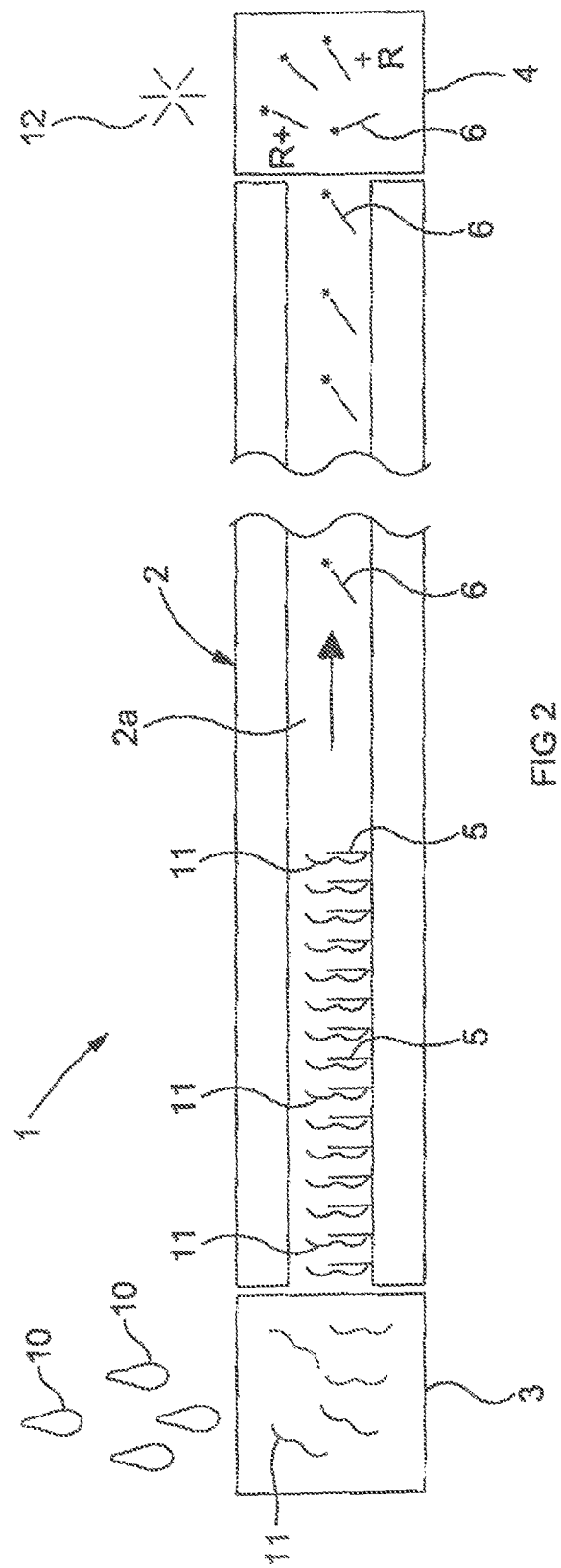
FIG. 2 illustrates use of the device shown in FIG. 1 detecting a target nucleic acid in a sample.

The liquid sample to be analysed is shown in FIG. 2 as being applied as drops to the sample receiving station 2 from where it passes into the upstream end of the capillary tube 2 and then on to the detection region 4, as depicted by the arrow.

Nucleic acid strands 11 will displace labelled oligonucleotides 6 from the immobilised oligonucleotides 5 to which they are hybridised. This is ensured by the fact that the labelled oligonucleotides 6 do not have 100% sequence homology with the immobilised oligonucleotides 5 and are therefore preferentially displaced by target nucleic acid 11 present in the sample which does have a sequence with 100% homology to that of the immobilised oligonucleotides 5. Therefore target nucleic acid strands 11 become hybridised to the immobilised oligonucleotides 5 as shown.

Displaced, labelled oligonucleotides 6 that have passed beyond the downstream end of the collection of immobilised oligonucleotides 5 are carried by the capillary flow in the tube 2 to the detection region 4 where the label (on the oligonucleotide 6) and the reagent provided at the detection region 4 (capable of interacting with the label) together produce a detectable signal which confirms the presence of the nucleic acid strands 10 in the sample being assayed. In preferred embodiments of the invention, the label and the reagents will together interact to produce a light signal depicted generally as 12, the emission, or production, of which may be checked for electronically to confirm the results of the diagnosis.

The intensity of the signal generated is dependent on the number of molecules of labelled oligonucleotide 6 compared to the number of molecules of target nucleic acid in the sample, provided that the latter does not exceed the former. For the purposes of a simplified explanation, reference is made to the assay device 1 shown in FIG. 1 for which there are nine labelled oligonucleotides 6. If the analyte contains, say, four target nucleic acid strands then (in an idealised case) four of the labelled oligonucleotides 6 will reach the detection region 4. Similarly if the sample to be analysed contains, say, seven target nucleic strands then correspondingly seven of the labelled oligonucleotides 6 will reach the detection region, thus providing a more intense signal than in the case where there were four target nucleic acid strands in the sample. Similarly nine target nucleic acid strands in the sample then nine labelled oligonucleotides 6 will reach the detection region, thereby giving rise to a more intense signal than the first two cases. If the sample contains more than nine target nucleic acid strands then it will still be the case that "only" nine of the labelled oligonucleotides will reach the detection region. It will thus be appreciated that the number of labelled oligonucleotides 6 should be "tailored" so as to exceed the maximum number of anticipated target nucleic acid strands, particularly if the assay device is to be used for quantitative work.

Figure 3:
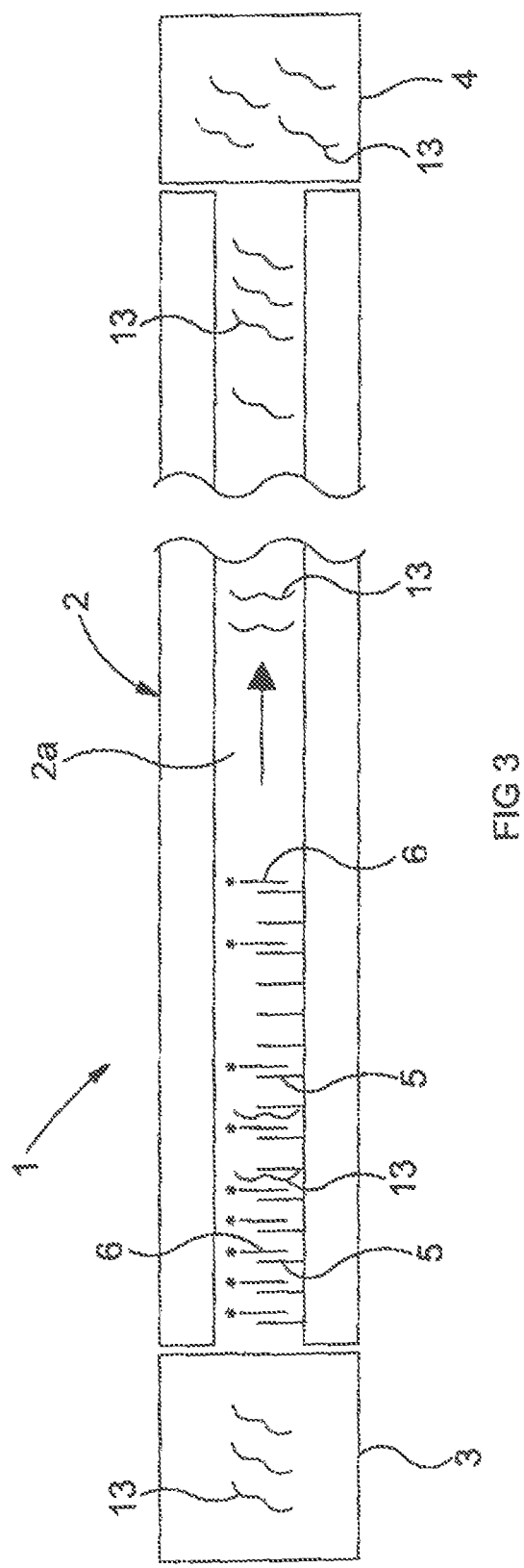
FIG. 3 illustrates the manner in which the device shown in FIG. 1 avoids "false positives" in an assay procedure.

A very important feature of the device is its ability that it does not give rise to "false positives" (i.e. a result suggesting that the nucleic acid being assayed is present in the sample when it is not. This important feature results from the presence of the immobilised oligonucleotides 5 at (in the original assay device) do not have a labelled oligonucleotides 6 hybridised thereto. This advantage is illustrated schematically in FIG. 3, for which it is assumed that the sample being analysed contains nucleic acid 13 which is not the particular nucleic acid 10 of interest and there is no such nucleic acid 10 present in the sample. In this case, there is the possibility that the nucleic acid 13 will displace some of the labelled oligonucleotides 6 from the immobilised oligonucleotides 5 to which they were originally hybridised. However these displaced, labelled oligonucleotides 6 will be captured by immobilised oligonucleotides 5 in the sub-collection thereof that were not originally hybridised to labelled oligonucleotides 6. Statistically the chances of nucleic acid 13 displacing labelled oligonucleotides 6 is relatively low (although not zero). Consequently it is overall much more likely that any displaced, labelled nucleotide 6 will be re-captured by immobilised oligonucleotides 5 and be retained thereon so as not to pass to the detection region 4. As a result, no signal is generated at that region and false positives are avoided.

Generally there will be numerically more of the immobilised oligonucleotides 5 than the number of strand of target nucleic acid sequence 10 that would be anticipated to be present in the sample being assayed. Typically the fraction of the fraction of the immobilised oligonucleotides 5 to which are hybridised the labelled oligonucleotide 6 will be from 50-90%.

The oligonucleotides 5 and 6 may without limitation be DNA, RNA mRNA or PNA The illustrated device may be used for the detection of various medical conditions characterised by the presence of a specific nucleic acid sequence in a sample taken from a patient. Thus, for example, the device may be used for determining whether or not a particular bacteria is present in the sample taken from the patient. As a development of this possibility, the device may also be used for testing whether the bacteria is present in a "live" or "dead" form. The use of DNA of appropriate sequence for the immobilised oligonucleotides 5 and labelled DNA oligonucleotides 6 can be used to determine whether or not the bacteria is present in the sample, but will not indicate whether or not the bacteria is in a "live" or "dead" form. The use of mRNA of appropriate sequence for the immobilised oligonucleotides 5 and labelled mRNA oligonucleotides 6 can be used to determine whether the bacteria present in the sample is in a "live" form since a positive signal resulting from mRNA capture confirms that the bacteria is alive, i.e it is producing proteins and thus distinguishes between "live" and "dead" forms of the bacteria. A negative mRNA result indicates that the bacteria is not alive. Thus from two tests the bacterial presence can be determined and that it is active or not.

Reference is now made to FIG. 4 which illustrates an alternative embodiment of assay device in accordance with the invention. This embodiment is intended for use in detecting whether a particular antigen is present in a sample taken from a patient and to this end the immobilised oligonucleotides 5 (of the device of FIG. 1) are replaced by immobilised antibodies 45 and the labelled oligonucleotide 6 (of the device of FIG. 1) are replaced by labelled antigens 46, the device 41 further comprising a capillary tube 42 (with a capillary bore 42a), sample receiving station 43 and detection region 44 which are respectively equivalent to the capillary tube 2, sample receiving station 3 and detection region 4 of the device of FIG. 1. The antibodies 46 are specific to the antigen to be detected in the sample taken from the patient. The labelled antigens 46 (apart from their label) identical with the antigens in the sample to be detected. The relative numbers of the immobilised antibodies 45 and the labelled antigens 46 may be the same as discussed in relation to FIG. 1 for the relative numerical amounts of the immobilised oligonucleotides 5 and label oligonucleotides 6.

The assay device 41 illustrated in FIG. 4 may be used for detecting a particular disease as characterised by the presence of a particular antigen (e.g. a virus) in a sample taken from the patient. A further use of the device illustrated in FIG. 1 is to monitor the effectiveness of a particular therapy being used to treat an infection caused by a particular bacteria or virus. In this case, the device is used quantitatively to determine relative amounts (greater, lower etc) of the particular antigen in samples taken over a period of time from the patient under investigation. If the intensity of the detected signal goes down over time then this demonstrates reducing amounts of the antigen with increasing time and thus confirms effectiveness of the treatment.

It may be the case that biological samples to be assayed by devices in accordance with the invention incorporate extraneous matter which is ideally removed before the liquid sample passes to the region of the immobilised oligonucleotides 5 and labelled oligonucleotides 6 (in the case of the device of FIG. 1) or the immobilised antibodies 45 and labelled antigens 46 (in the case of the device of FIG. 4). Whilst it is possible to undertake some preparation of the sample before it is applied to the sample receiving station, FIG. 5 illustrates a convenient modification to the illustrated devices which avoids the need for such separate sample preparation. The arrangement of FIG. 5 may be applied to either the assay device of FIG. 1 or assay device 41 of FIG. 4. However for convenience the arrangement will be described principally in relation to FIG. 1 with the corresponding parts of FIG. 4 being given in parentheses. In the device 1 (41) of FIG. 5, there is a sample treatment region 51 which is provided between the sample receiving station 3 (43) and the upstream end of the capillary tube 2 (42). Sample treatment region 51 has a column matrix 52 selected to apply a particular treatment to a sample moving from the sample receiving station 1 (41) into the capillary tube 2 (42) via capillaries 53 and 54. The "column matrix" may, for example, be an ion-exchange resin (dependent on the nature of the sample the column matrix could be either anion or cation exchanger) or size exclusion, matrix for example only Sephadex G10 which will retain particles and salts.

Although FIGS. 1-5 describe the invention with reference to a single capillary tube 2 (FIG. 1) or 42 (FIG. 4) it will generally be the case that such a capillary tube is associated with a "control capillary tube" in which no immobilised "first binding partners" (e.g. oligonucleotides 5 or antibodies 45) or "labelled second binding partners" (i.e. labelled oligonucleotides 6 or labelled antigens 46) are provided. An assay carried out using a capillary tube 2 or 42 will be run in parallel with the "control capillary" and the results at the detection regions of both capillary tubes compared to establish the difference in signal provided by the "assay" capillary tube and the "control" capillary tube.

FIG. 6 illustrates a moulded body 61 for use in producing an assay device in accordance with the invention with both "assay" and "control" capillary tubes. Body 61 is of generally cuboid configuration and has a major face (the upper face illustrated in FIG. 6) formed with two open-topped channels 62*a* and 62*c*, a single well 63 and two further wells 64. Channel 62*a* is intended for forming an "assay" capillary tube and channel 62*c* is intended for forming a "control" capillary tube. Well 63 is provided at the upstream ends of channel 62*a* and 62*c* and is connected by these two channels to respective ones of the wells 64. It will be appreciated that well 63 and wells 64 are for use in forming a sample receiving station 3 and two detection regions 4 (one for the "assay" capillary tube and the other for the "control" capillary tube).

Body 61 is comprised of an optically transparent, plastics material (preferably polycarbonate). The use of polycarbonate allows an optically clear region in the moulded plastic device at the locations of the wells 64 which (as indicated above) are used in forming detection regions. As a first step in producing a device in accordance with the invention from the body 61 shown in FIG. 1, it is necessary that the body 61 (and particularly its open-top channel 62*a* and 62*c*) be thoroughly cleaned to remove any remaining mould release agents or other contaminants (particularly hydrophobic contaminants) which may hinder the flow of an aqueous liquid along a capillary tube ultimately formed from the open-topped channels 62*a* and 62*c*. Such washing may be with water and detergents. By way of example, the channels may be cleaned by washing with SDS (1-10% in distilled water), drying under a nitrogen atmosphere, subsequently washing with water and absolute ethanol, and finally drying under a nitrogen atmosphere.

Once body 61 has been thoroughly cleaned (and assuming that a device of the type illustrated in FIG. 1 is to be produced) the open-topped channels may be provided with the immobilised oligonucleotides 5 and the labelled oligonucleotides 6. For this purpose, the surface of the channel 62*a* (or at least the region thereof on which the oligonucleotides 5 are to be immobilised) may be treated to provide epoxy groups on the surface thereof. This may be effected, for example, by treatment of the surface with a glycidoxy compound of the formula:

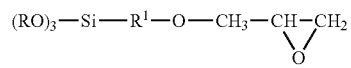

where R is an alkyl group of 1 to 4 carbon atoms and R' is an alkylene residue. Most preferably R is methyl and R' is $-(CH_2)_3-$.

By way of example only, the following procedure may be used for immobilisation of an oligonucleotide by its 5' end.

The channels have applied thereto 5-20 µl of 3-glycidoxypropyl trimethoxy silane and are held at 50° C. for three hours under nitrogen. Subsequently the channels are washed with dry methanol and dry ether, under nitrogen. Cross linking is then performed at 50° C. for greater than 2 hours under nitrogen. Free hydroxyl groups may be capped with 20 µl of trimethyl chlorosilane in pyridine or similar anhydrous solvent solution for 2 hours at room temperature. The channels are then washed as described above. Oligonucleotides with a 5'-iodo-5'-deoxythymidine are reacted with sodium triphenyl methylmercaptile in DMF to produce an S-trityl compound. This is further reacted with diisopropylammo tetrazolide and 2-cyanoethoxy bis N,N-diisopropylamino phosphate in DCM to produce the cyanoethyl. The S-trityl group is removed by reduction methods known in the art (Connolly, Nucleic acid Research, 16, 9, 1988) before linking with the epoxy substituted channel using sodium hydride. In anhydrous DMF to effect condensation of the oligonucleotide to the epoxy group.

Alternatively the oligonucleotide may be immobilised by its 3' end using the following procedure.

The sodium salt of a DMT oligonucleotide can be prepared by dissolving the oligonucleotide in anhydrous DMF (dried over $P_2O_5$) under nitrogen with the addition of sodium hydride (1 gram/10 ml). The sodium hydride is then filtered off and the sodium salt of the oligonucleotide is reacted with the epoxy group in the channel. In anhydrous DMF Further details of the above immobilisation chemistry are disclosed, for example, in U.S. Pat. No. 5,910,406 (Tepnel).

In the case of either 3'- or 5'-immobilisation, the channels may then be washed with distilled water followed by washing in anhydrous ethanol and dried under nitrogen.

The second binding partner is dissolved in hybridisation buffer 2×SSC (300 mM sodium chloride 30 mM sodium citrate) and 0.1-0.9 molar ratio (compared to the immobilised oligonucleotide) is applied to the second channel and incubated at 20-40° C. for two hours. The channels are then washed in distilled water and ethanol under nitrogen. A pad of absorbent material (e.g. Whatman filter paper such as Whatman Grade GF/B Glass Microfiber Filters) is then applied to the sample well. If required, the pad may be pre-impregnated with any reagents required for the analysis.

For certain embodiments of the invention, an absorbent pad (e.g. of the type described above) impregnated with a reagent system for developing a signal from the label may be introduced into the wells 64a and 64c to form detection regions for the device. Thus, in the case that the label is an enzyme requiring a substrate then a further pad of Whatman filter paper impregnated with the substrate for the enzyme is introduced into the wells 64a and 64c at the distal end of the capillaries. For other embodiments of the invention, e.g. In the case of fluorescence or chemiluminescence detection, the wells 64a and 64c remain free of paper to allow signal detection. Thus, for example, in the case of where the label is Horse Raddish Peroxidase, the well may contain luminol dried in situ as the substrate for the enzyme. In the case where the label is acridinium ester, the wells remain empty with the signal being provided by the acridinium ester per se. The channels are then sealed with tape or a plastic cover with UV curing adhesive forming closed capillaries.

The arrangement of FIG. 7 comprises a bank of three assay devices 71 each produced from a body 61 of the type illustrated in FIG. 6 and produced from optically transparent plastics material. These assay devices 71 each comprise an assay capillary tube 72a, a control capillary tube 72c, a sample receiving station (not illustrated in FIG. 7 but referenced as 73 for convenience) and detection regions 74a and 74c for the assay capillary tube 72a and control capillary tube 72c respectively. Each assay capillary 72a is such as to assay for a different (potential) characteristic of a particular sample. Thus, for example, the assay capillary 72a of one device 71 may have immobilised oligonucleotides 5 with labelled oligonucleotides 7 hybridised thereto (as described with reference to FIG. 1) to assay for the presence of a particular nucleic acid sequence in a sample. Another one of the assay devices 71 may have, in its assay capillary 72a, immobilised antibodies 45 with labelled antigen 46 bound thereto (as described with reference to FIG. 4). The remaining assay device 71 may, for example, be such as to test for a different nucleic acid sequence, a different antigen or another characteristic as desired. The labels used in the assay devices 71 are such as to produce a light signal with reagent present at the detection regions 74a and 74c.

The arrangement shown in FIG. 7 additionally comprises a sample distribution unit 80 and a detector unit 90. Sample distribution unit 80 is structured so as to be capable of receiving, and supporting, three of the assay devices 71. The devices 71 are received in the unit 80 at their upstream ends, as illustrated in FIG. 7, so that their sample receiving stations 73 are sealed within the unit 80. The sample distribution unit 80 has a sample inlet 81 and is internally configured (not shown) so that liquid sample introduced through the inlet 81 is transferred to the sample receiving stations 73 of all three assay devices 71. A vent 82 is further provided for unit 80 so as to release excess pressure caused by the introduction of sample into the unit.

Detector unit 90 has three sets (only one shown) of four fibre optic light pipes 91a-d, each set being associated with a respective one of the assay devices 71. For convenience, only one set of the four light pipes 91a-d has been shown and this is for the uppermost of the three assay devices 71 shown in FIG. 1. Light pipes 91a and 91b lead into the upper regions of detection zones 74a and 74c respectively. Light pipes 91a and 91b are associated with a light source (not shown) in the detector which passes light along these pipes 91a and 91b into the top of detection regions 74a and 74b. In contrast, light pipes 91c and 91d lead from the detector 90 to the undersurfaces of detection regions 74a and 74c of the uppermost assay device 71. Each light pipe 91c and 91d is associated with a light detector (not shown) provided within the detection device.

For the purposes of carrying out an assay, liquid sample is introduced through the inlet 81 of distribution unit 80 and the assay devices 71 function as previously described. Light that has passed from light pipes 91a and 91b into and through detection regions 74a and 74b is collected by the light pipes 91c and 91d respectively and fed back to the detector 90. Detector 90 is programmed to detect any colour change in the light that has been passed along light tube 91a and collected by light tube 91c. Any such colour change is compared with the result from detection region 74c (control). Given there is a difference in colour change between detection region 74a (assay) and detection region 74c (control) then this is a "positive" result for the assay.

Although FIG. 7 has been described with reference to signal detection by light transmission (the detection regions being optically transparent) it will be appreciated that signal detection may also by reflectance, particularly in the case where the detection region incorporates an absorbent pad impregnated with a substrate for an enzyme.

A number of modifications may be made for the illustrated embodiments. For example, in the arrangement of FIG. 7 the detector unit 90 is shown as a separate unit. It would however also be possible to produce an assay device in accordance with the invention incorporating its own detection unit. Power for such an "on-board" detection unit could, for example, be provided by a battery. Alternatively a power source for such a device may be as described in WO 00/33063 (Moorlodge Biotech Ventures Limited), in which case the power source will comprise at least one pair of electrodes of dissimilar materials provided on the device and arranged such that travel of an aqueous liquid sample between the electrodes causes a current to be generated for operating the detection arrangement. The dissimilar materials may comprise carbon or one or more metals, e.g. copper and zinc. The electrodes of one material may be interdigitated with those electrodes of another dissimilar material such that current, in the presence of liquid sample, may flow from one electrode to another.

In a further proposed modification, again applicable to the arrangement shown in FIG. 7, the sample receiving region 73 may be emitted and the capillary tube 62a and 62c simply be open at their upstream ends. In this case, the liquid distribution arrangement 80 may comprise a sponge (or other absorbent material) provided at its interior, rear surface. On insertion of the assay device 7 into the distribution 8, the upstream end of the assay device 71 pushes into, and compresses, the sponge or other resilient material allowing the upstream ends of the capillary tube 62a and 62c to come into contact therewith. For carrying out the assay, the sponge is impregnated with the liquid sample to be assayed, this liquid sample then passing into the capillary tubes 62a and 62c for analysis as described more fully above.

FIG. 8 shows plan and side views of a further embodiment of assay device in accordance with the invention. This device is made of polycarbonate and has two serpentine capillaries (with five linear sections) each of which runs from an upstream sample well to a respective collection well containing a reagent system of the type described more fully above. Light pipes are associated with each collection wee for the purpose of signal detection.

By way of example, each capillary may have a total length of about 342 mm. The individual capillaries may be of triangular cross-section with each side having a length 0.4 mm. Each capillary has an approximate volume of 30 µl.

Although the invention has been described with specific reference to an assay device having one "assay capillary" and one "control capillary" it will be appreciated that the device could include two or more "assay capillaries" and if necessary two or more "control capillaries". Each such "assay capillary" could be such as to perform the same or different assay on a sample.

The invention may be applied to the mass screening of sample and data about the results collected electronically for onward transmission to medical authorities who (from data supplied from a number of locations) can determine the spread of an infection and/or coordinate medical supplies for dealing with the infection.

The invention will be illustrated by the following, non-limiting Examples.

Example 1

This Example describes the preparation of polycarbonate substrates having amino groups to which binding partners may be immobilised.

The procedure of this Example was effected on polycarbonate substrates ("platforms") having a size of about 75 mm×25 mm×3 mm formed along their length with two open-topped, triangular section capillary channels each of serpentine configuration with five linear capillary pathways between the upstream and downstream ends of the serpentine the triangular section channels had sides of 0.4 mm length. Each channel had a total length of about 342 mm and a volume of about 30 µl.

The platforms were initially nitrated by full emersion in 30% aqueous nitric acid solution at 80° C. for 3 hrs. Subsequent to this nitration reaction, the platforms were thoroughly washed with distilled water and air dried.

In the next step of the procedure, the platforms were treated with a 10% $NaSH_4$ w/v ethanol solution overnight at room temperature to effect reduction of the nitro groups to amino groups.

The platforms were then washed several times in distilled water, ethanol and Lectin Buffer (4M NaCl, 10 mM Tris, pH7.2, 10 mM $CaCl_2$, 10 mM $MnCl_2$) with air drying between washes. Finally, the platforms were air dried.

Example 2

This Example describes production of an assay device in accordance with the invention in which yeast mannoprotein is immobilised within the capillary of a polycarbonate substrate and has labelled Concavalin A displaceably bound thereto.

Step 1

Aminated polycarbonate platforms prepared in accordance with the procedure of Example 1 were reacted with an aqueous solution of 5 mM N-(3-dimethylaminopropyl)-N-ethylcarbodiimide hydrochloride), 0.33 mM N-hydroxysulfosuccinimide sodium salt 5 mM 11-mercaptoundecanoic acid in a 0.1M MES buffer pH6.5 for 3 hrs and subsequently washed in Lectin Buffer. (MES is an abbreviation for the compound 2-(N-morpholino)ethanesulfonic acid).

After air drying, 1 mg/ml yeast mannoprotein (in Lectin Buffer) was added to the capillaries in a humid atmosphere at 4° C. and the substrate was allowed to stand overnight. The platforms were then washed in Lectin Buffer.

This procedure produced polycarbonate platforms in which yeast mannoprotein was immobilised in the capillaries.

Step 2

This step describes the displaceable binding of labelled Concavalin A to the immobilised yeast mannoprotein of the polycarbonate platforms produced in the previous step. The label used was Horse Radish Peroxidase (HRP).

Concavalin A was biotinylated according to manufacturer's instructions (BiotinTag micro biotinylation kit, Sigma). Avidin-HRP was part of the kit. A 30 µl mix of biotinylated Concavalin A/avidin-HRP/Lectin Buffer at 10/5/85 ratios was added on the capillary for 2 hrs at RT in a humidified atmosphere. The treated platforms were then washed in Lectin Buffer and air dried.

An assay device in accordance with the invention was prepared by affixing adhesive plastics tape (water resistant adhesive) over the top of the capillary channels to complete the capillary tubes for the device.

Example 3

This Example describes production of an assay device in accordance with the invention in which yeast mannoprotein is immobilised within the capillary of a polycarbonate substrate and has labelled Concavalin A displaceably bound thereto.

Step 1

Aminated polycarbonate platforms prepared in accordance with the procedure of Example 1 were reacted with an aqueous solution of 5 mM N-(3-dimethylaminopropyl)-N-ethylcarbodiimide hydrochloride), 0.33 mM N-hydroxysulfosuccinimide sodium salt 5 mM 11-mercaptoundecanoic acid in a 0.1M MES buffer pH6.5 for 3 hrs and then washed in Lectin Buffer.

After air drying, 1 mg/ml yeast mannoprotein (in an aqueous solution of 5 mM N-(3-dimethylaminopropyl)-N-ethylcarbodiimide hydrochloride), 0.33 mM N-hydroxysulfosuccinimide sodium salt in a 0.1M MES buffer pH6.5 was added to the capillaries in a humidified atmosphere at 4° C. and the platforms were allowed to stand overnight.

The treated platforms were washed in Lectin Buffer and air dried.

This step produced polycarbonate platforms in which yeast mannoprotein was immobilised in the capillaries.

Step 2

Using the procedure of Step 2 of Example 2, HRP-labelled Concavalin A was displaceably bound to the immobilised yeast mannoprotein of the platforms produced in accordance with Step 1 of this Example.

An assay device in accordance with the invention was prepared by affixing adhesive plastics tape (water resistant adhesive) over the top of the capillary channels to complete the capillary tubes for the device.

Example 4

This Example describes production of an assay device in accordance with the invention in which yeast mannoprotein is immobilised within the capillary of a polycarbonate substrate and has labelled Concavalin A displaceably bound thereto.

Step 1

Aminated polycarbonate platforms produced in accordance with the procedure of Example 1 were reacted with an aqueous solution of 5 mM N-(3-dimethylaminopropyl)-N-ethylcarbodiimide hydrochloride), 0.33 mM N-hydroxysulfosuccinimide sodium salt 5 mM 11-mercaptoundecanoic acid in a 0.1M MES buffer pH6.5, also containing 1 mg/ml yeast mannoprotein in a humidified atmosphere at 4° C. and allowed to stand overnight.

The treated platforms were then washed with Lectin Buffer and air dried.

The procedure of this Step produced polycarbonate platforms in which yeast mannoprotein was immobilised in the capillaries.

Step 2

Using the procedure of Step 2 of Example 2, HRP-labelled Concavalin A was displaceably bound to the yeast mannoprotein in the capillaries.

An assay device in accordance with the invention was prepared by affixing adhesive plastics tape (water resistant adhesive) over the top of the capillary channels to complete the capillary tubes for the device.

Example 5

This Example describes testing of the assay devices (with displaceably bound HRP-labelled Concavalin A) produced in accordance with Examples 2, 3 and 4 for displacement of the Concavalin A by either (i) a 20 mg/ml yeast mannoprotein as a solution in Lectin Buffer, or (ii) 2 mg/ml polystyrene beads (in Lectin Buffer) on which yeast mannoprotein had been immobilised.

The beads for test (ii) were prepared by the following procedure.

Protein Immobolisation on Carboxylated Polystyrene Beads

50 μl of 10% solid to liquid carboxylated polystyrene 5 micron beads (Polymer labs) solution was washed once in 1 ml of Lectin Buffer and then centrifuged (13,000 rpm 5 mins). Supernatant was removed and the beads were diluted in 1 ml of an aqueous solution of 75 mM N-(3-dimethylaminopropyl)-N-ethylcarbodiimide hydrochloride), 15 mM NHSS (N-hydroxysulfosuccinimide sodium salt) and 50 mM PBS at pH 7.3 with 2 mg/ml of yeast mannoprotein. The mix was shaken at room temperature for 3 hrs and then washed; supernatant was then removed and the beads were further washed in Lectin Buffer prior to being separated by centrifugation (13,000 rpm 5 mins). The beads were taken up in 1 ml of Lectin Buffer and kept at 4° C.

Assay Procedure

The samples (i) 20 mg/ml yeast mannoprotein, and (ii) 2 mg/ml beads with conjugated yeast mannoprotein (both in Lectin Buffer) and were run by capillary action on the platforms produced in accordance with Examples 2, 3 and 4.

Liquid was allowed to run along the capillary pathway and 5 μl were collected from the end of the capillary and added to 30 μl of HRP substrate (from DRG Diagnostics estradiol ELISA kit) in an eppendorf. Colour was allowed to develop and samples were read at a spectrophotometer.

The results are shown in the following Table:

| | Sample loaded on platform (1 ml), and absorbance at 446-456 nm | | |
|---|---|---|---|
| Example No. | Lectin Buffer | 20 mg/ml Yeast mannoprotein | 2 mg/ml Yeast mannoprotein conjugated beads |
| 2 | No peak | Weak Colour | 3.000 (456 nm) |
| 3 | No peak | 2.699 (448.5 nm) | 2.224 (446 nm) |
| 4 | No peak | 2.501 (446 nm) | Over 4.000 (446 nm) |

The results demonstrate that the yeast mannoprotein in the samples being assayed (i.e. samples (i) and (ii)) was able to displace the Concavalin A that had been display sampling bound to the yeast mannoprotein that had been immobilised in the capillary pathway. Overall, the best results were obtained with the polycarbonate platform produced in accordance with Example 4. In particular, the assay run on this platform using the yeast conjugated beads provided the best signal of all six combinations tested. The signal was considerably improved as compared to the assay run, on that platform, using the 20 mg/ml solution of yeast mannoprotein, thus demonstrating signal amplification.

Example 6

This Example provides a further demonstration of signal amplification A number of assay devices were prepared as described in Example 4 and filter paper saturated in HRP substrate and air dried was placed at the end of the capillary The following five test analytes were run on the devices using the assay:
1. 2 mg/ml polystyrene beads with immobilised yeast mannoprotein, prepared as described in Example 5.
2. 2 mg/ml polystyrene beads with immobilised Concavalin A, prepared as described in Example 5. but substituting 2 mg/ml Concavalin A for the yeast mannoprotein.
3. 2 mg/ml of free yeast mannoprotein
4. 2 mg/ml free Concavalin A
5. 2 mg/ml unconjugated beads,
6. lectin buffer Both mannoprotein and Concavalin A conjugated to beads (ie test analytes 1 and 2) produced a visible blue signal on the filter paper, whereas free yeast mannoprotein, free Concavalin A, unconjugated beads and lectin buffer did not.

Example 7

This Example demonstrates production of a polycarbonate platform in which an Oligonucleotide is immobilised in the capillary and has a labelled Oligonucleotide bound thereto.

Polycarbonate platforms were prepared using the procedure described in Example 1.

The aminated platforms were immersed in a solution of 5% glutaraldehyde v/v (0.1M PBS, pH6.5) and 5% Trimethylaminoborane in a beaker and placed in an ultrasonic bath for 2 hours at room temperature. The platforms were then washed extensively with ethanol and air dried.

*Neisseria meningitides* 5'NH ATTTTAATTAC-GAAGGCTACGCATT 3' (SEQ ID NO: 16) were dissolved in 0.1M carbonate buffer pH 9.0 (0.1-10 um). 20 μl of the solution was applied to the capillaries on the platform and allowed to react for 4 hours at room temperature in a wet atmosphere.

The platforms were then washed once in PBS and air dried.

The presence of the immobilised oligonucleotide was determined by applying an enzyme (alkaline phosphatase) labelled second oligonucleotide, for *Neisseria meningitides* 5' Alkaline Phospatase GGAATTAATGCGTAGCCT-TCGTAATTAAAAT3' (SEQ ID NO: 17) were added to the sample platform. Equimolar second oligonucleotide was incubated in the capillary for 10 minutes at room temperature in 1×SSC. The platform was then washed with 1×SSC. (A 20× stock solution consists of 3M sodium chloride and 300 mM trisodium citrate (adjusted to pH7.0 with HCl.)

Substrate for Alkaline Phosphatase (NBT/BCIP) was the added to the capillary and a colour developed, demonstrating that the reaction was complete (linkage and hybridisation).

The invention claimed is:

1. A method of assaying a liquid sample for determining the presence and/or amount of a target nucleic acid analyte present or potentially present in the sample, the method comprising the steps of:
   (a) providing a capillary tube having immobilised therein a collection of first binding partners which comprise nucleic acid sequences capable of specifically binding to the analyte, said capillary tube further incorporating a collection of second binding partners which comprise nucleic acid sequences displaceably bound to a fraction of said first binding partners wherein 10-90% by mole of said first binding partners have said second binding partners bound thereto whereby there are free first binding partners immobilised within the capillary tube, said second binding partners having a label and being displaceable from the first binding partners by the analyte to be detected;
   (b) causing the liquid sample to flow from an upstream end of the capillary tube to a downstream end thereof; and
   (c) detecting for the presence of the label at the downstream end of the capillary tube.

2. A method as claimed in claim 1 wherein 50-70% by mole of said first binding partners have said second binding partners bound thereto.

3. A method as claimed in claim 1 wherein the first binding partners are covalently immobilised within the capillary tube.

4. A method as claimed in claim 1 wherein the nucleic acid sequences of the first binding partners and the nucleic acid sequences of the second binding partners comprise DNA, mRNA, RNA or PNA sequences.

5. A method of assaying a liquid sample for determining the presence and/or amount of an analyte present or potentially present in the sample, the method comprising the steps of:
   (a) providing a capillary tube having immobilised therein a collection of first binding partners which comprise a polysaccharide capable of specifically binding to the analyte, said capillary tube further incorporating a collection of second binding partners which comprise a lectin displaceabley hybridised to a fraction of said first binding partners wherein 10-90% by mole of said first binding partners have said second binding partners bound thereto whereby there are free first binding partners immobilised within the capillary tube, said second binding partners having a label and being displaceable from the first binding partners by the analyte to be detected;
   (b) causing the liquid sample to flow from an upstream end of the capillary tube to a downstream end thereof; and (c) detecting for the presence of the label at the downstream end of the capillary tube.

6. A method as claimed in claim 5 for the detection of an organism having surface lectins capable of displacing the labelled, lectin second binding partner.

7. A method as claimed in claim 5 wherein 50-70% by mole of said first binding partners have said second binding partners bound thereto.

8. A method as claimed in claim 5 wherein the first binding partners are covalently immobilised within the capillary tube.

\* \* \* \* \*

SEQUENCE LISTING

<160> NUMBER OF SEQ ID NOS: 17

<210> SEQ ID NO 1
<211> LENGTH: 25
<212> TYPE: DNA
<213> ORGANISM: Unknown
<220> FEATURE:
<223> OTHER INFORMATION: Oligonucleotide

<400> SEQUENCE: 1
attttaatta cgaaggctac gcatt                                              25

<210> SEQ ID NO 2
<211> LENGTH: 25
<212> TYPE: DNA
<213> ORGANISM: Unknown
<220> FEATURE:
<223> OTHER INFORMATION: Oligonucleotide

<400> SEQUENCE: 2
gggacacccg cgaagttttg gaagc                                              25

<210> SEQ ID NO 3
<211> LENGTH: 25
<212> TYPE: DNA
<213> ORGANISM: Unknown
<220> FEATURE:
<223> OTHER INFORMATION: Oligonucleotide

<400> SEQUENCE: 3
ctgtcagttg tctcgtgcat tgtca                                              25

<210> SEQ ID NO 4
<211> LENGTH: 25
<212> TYPE: DNA
<213> ORGANISM: Unknown
<220> FEATURE:
<223> OTHER INFORMATION: Oligonucleotide

<400> SEQUENCE: 4
gttgcgggct gttgcgtcgg aaacc                                              25

<210> SEQ ID NO 5
<211> LENGTH: 25
<212> TYPE: DNA
<213> ORGANISM: Unknown
<220> FEATURE:
<223> OTHER INFORMATION: Oligonucleotide

<400> SEQUENCE: 5
atggataagc gcgaccagtt cgccg                                              25

<210> SEQ ID NO 6
<211> LENGTH: 24
<212> TYPE: DNA
<213> ORGANISM: Unknown
<220> FEATURE:
<223> OTHER INFORMATION: Oligonucleotide

<400> SEQUENCE: 6
gatgtgtttg gcaatcatgg cttg                                               24

<210> SEQ ID NO 7
<211> LENGTH: 24
<212> TYPE: DNA
<213> ORGANISM: Unknown

-continued

```
<220> FEATURE:
<223> OTHER INFORMATION: Oligonucleotide

<400> SEQUENCE: 7
cacaagtgat gcgtccgagc gtaa                                            24

<210> SEQ ID NO 8
<211> LENGTH: 22
<212> TYPE: DNA
<213> ORGANISM: Unknown
<220> FEATURE:
<223> OTHER INFORMATION: Oligonucleotide

<400> SEQUENCE: 8
gagaaccaga ctaaagtttc aa                                              22

<210> SEQ ID NO 9
<211> LENGTH: 22
<212> TYPE: DNA
<213> ORGANISM: Unknown
<220> FEATURE:
<223> OTHER INFORMATION: Oligonucleotide

<400> SEQUENCE: 9
aaaaaacggt caaagcggag tc                                              22

<210> SEQ ID NO 10
<211> LENGTH: 21
<212> TYPE: DNA
<213> ORGANISM: Unknown
<220> FEATURE:
<223> OTHER INFORMATION: Oligonucleotide

<400> SEQUENCE: 10
acagatactg ccttctcttg g                                               21

<210> SEQ ID NO 11
<211> LENGTH: 20
<212> TYPE: DNA
<213> ORGANISM: Unknown
<220> FEATURE:
<223> OTHER INFORMATION: Oligonucleotide

<400> SEQUENCE: 11
atctgcagca ggtttcgtgg                                                 20

<210> SEQ ID NO 12
<211> LENGTH: 18
<212> TYPE: DNA
<213> ORGANISM: Unknown
<220> FEATURE:
<223> OTHER INFORMATION: Oligonucleotide

<400> SEQUENCE: 12
caggctgcgt ggcgtttt                                                   18

<210> SEQ ID NO 13
<211> LENGTH: 26
<212> TYPE: DNA
<213> ORGANISM: Unknown
<220> FEATURE:
<223> OTHER INFORMATION: Oligonucleotide

<400> SEQUENCE: 13
acaaaatctt ctgattttaa tacagc                                          26
```

```
<210> SEQ ID NO 14
<211> LENGTH: 24
<212> TYPE: DNA
<213> ORGANISM: Unknown
<220> FEATURE:
<223> OTHER INFORMATION: Oligonucleotide

<400> SEQUENCE: 14 tcttttcct aacaccgctt tgaa                                          24

<210> SEQ ID NO 15
<211> LENGTH: 24
<212> TYPE: DNA
<213> ORGANISM: Unknown
<220> FEATURE:
<223> OTHER INFORMATION: Oligonucleotide

<400> SEQUENCE: 15
aacactgctt tggatcgagc tgtg                                         24

<210> SEQ ID NO 16
<211> LENGTH: 25
<212> TYPE: DNA
<213> ORGANISM: Neisseria meningitidis

<400> SEQUENCE: 16
attttaatta cgaaggctac gcatt                                        25

<210> SEQ ID NO 17
<211> LENGTH: 31
<212> TYPE: DNA
<213> ORGANISM: Unknown
<220> FEATURE:
<223> OTHER INFORMATION: Oligonucleotide

<400> SEQUENCE: 17
ggaattaatg cgtagccttc gtaattaaaa t                                 31
```